(12) United States Patent
Nashima et al.

(10) Patent No.: US 9,163,663 B2
(45) Date of Patent: Oct. 20, 2015

(54) ROTATING SHAFT HOLDING MECHANISM AND ROTATIONAL VISCOMETER WITH SAME

(75) Inventors: Takeshi Nashima, Tsukuba (JP); Yasuyuki Yamamoto, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 14/401,578

(22) PCT Filed: May 18, 2012

(86) PCT No.: PCT/JP2012/062789
§ 371 (c)(1),
(2), (4) Date: Feb. 16, 2015

(87) PCT Pub. No.: WO2013/171896
PCT Pub. Date: Nov. 21, 2013

(65) Prior Publication Data
US 2015/0159691 A1   Jun. 11, 2015

(51) Int. Cl.
*F16C 11/12* (2006.01)
*F16C 27/02* (2006.01)
(Continued)

(52) U.S. Cl.
CPC . *F16C 27/02* (2013.01); *F16C 1/02* (2013.01); *F16C 11/12* (2013.01); *G01N 11/14* (2013.01)

(58) Field of Classification Search
CPC ....................................................... F16C 11/12
See application file for complete search history.

(56) References Cited

U.S. PATENT DOCUMENTS

2003/0086751 A1*   5/2003   Culpepper ...................... 403/52
2012/0034027 A1*   2/2012   Valois ............................ 403/291

FOREIGN PATENT DOCUMENTS

JP   64-040088   3/1989
JP   05-087654   4/1993
(Continued)

OTHER PUBLICATIONS

International preliminary report on patentability of PCT/JP2012/062789, dated Nov. 27, 2014.
(Continued)

*Primary Examiner* — Thomas R. Hannon
(74) *Attorney, Agent, or Firm* — Kristina Castellano; Castellano PLLC

(57) ABSTRACT

A compact and high-precision rotating shaft holding mechanism is provided which can be utilized for a device that requires a small amount of rotation.

A rotating shaft holding mechanism includes a plurality of parallel spring links, each of the plurality of parallel spring links including: a movable side connected to a rotating shaft by a hinge at a connection point at a distance h radially away from a center of rotation of the rotating shaft; a plurality of deformable sides which are parallel to each other; hinges each of which connects one end of a corresponding one of the deformable sides to the movable side; and hinges each of which connects the other end of a corresponding one of the deformable sides to the stationary section, the effective length of each of the deformable sides being set to h to permit the rotating shaft, which is connected to the movable side by the hinge at the connecting point at the distance h radially away from the center of rotation of the rotating shaft, to rotate within a range of finite angles, the plurality of parallel spring links including at least two parallel spring links oriented in different directions. A rotational viscometer uses the rotating shaft holding mechanism.

4 Claims, 2 Drawing Sheets

(51) Int. Cl.
*G01N 11/14* (2006.01)
*F16C 1/02* (2006.01)

(56) References Cited

FOREIGN PATENT DOCUMENTS

| JP | 07-244057 | 9/1995 |
| JP | 2002-022867 | 1/2002 |
| JP | 2002-022868 | 1/2002 |
| JP | 2002-048696 | 2/2002 |
| JP | 2005-049214 | 2/2005 |
| JP | 2006-322714 | 11/2006 |

OTHER PUBLICATIONS

International Search Report of PCT/JP2012/062789, dated Jul. 24, 2012.

* cited by examiner

A: Movable section of parallel spring
B: Stationary section of parallel spring
D: Hinge
E: Hinges of parallel spring
O: Shaft

ROTATING SHAFT HOLDING MECHANISM AND ROTATIONAL VISCOMETER WITH SAME

CROSS REFERENCE TO RELATED APPLICATION

This application is a U.S. National Stage Application of PCT/JP2012/062789 filed on May 18, 2012, which is incorporated herein by reference in its entirety.

TECHNICAL FIELD

The present invention relates to a rotating shaft holding mechanism that can be utilized for mechanisms and devices, of those which require rotating shafts, which require only small amounts of rotation.

Further, the rotating shaft holding mechanism is the one that was devised to solve the problems in the field where high-precision torque measurement is required. In particular, the rotating shaft holding mechanism is intended to be utilized for torque measurement in a rotational viscometer or a rotational viscometer type rheometer (both of which are hereinafter referred to simply as "rotational viscometer"). Therefore, the present invention relates to a viscometer having a rotating shaft holding mechanism.

BACKGROUND ART

Conventionally, for many a rotating shaft, a structure such as a ball bearing in which rotating bodies are held have been used. This reduces the precision of the rotating shaft and the frictional resistance of the rotating shaft. However, the rotating bodies held in the bearing affect the precision of the rotating shaft and, furthermore, cause the resistance of rotation to fluctuate with the rotation of the shaft. In the case of a use where this poses a problem, especially in a case where high precision and low frictional resistance are required, an air bearing of a structure in which an air film is held is used (see Patent Literature 5). However, the air bearing has the drawbacks of requiring a high-pressure air source and, what is more, of being not so compactible and being therefore high in moment of rotation. Further, the pressure of air that is supplied to the air bearing can be a source of generation of torque in some cases, and is a matter that requires attention when the air bearing is used as a bearing for high-precision torque measurement. Meanwhile, there has conventionally been known a holding mechanism that permits an object in translational motion within a range limited by deformation of a spring (see Patent Literatures 1 to 4).

CITATION LIST

Patent Literature 1
Japanese Patent Application Publication, Tokukaihei, No. 07-244057 A
Patent Literature 2
Japanese Patent Application Publication, Tokukai, No. 2006-322714 A
Patent Literature 3
Japanese Patent Application Publication, Tokukai, No. 2002-022867 A
Patent Literature 4
Japanese Patent Application Publication, Tokukai, No. 2002-022868 A
Patent Literature 5
Japanese Patent Application Publication, Tokukai, No. 2005-049214 A

SUMMARY OF INVENTION

Technical Problem

It is an object of the present invention to provide an unconventional, novel rotating shaft holding mechanism by developing a structure in which deformation of a spring makes certain that devices, of those which require high-precision rotating shafts, which hardly rotate will rotate within a required range of finite angles.

This method can be used for static torque measurements, which do not require rotation (The rotating shaft needs to be fixed so that only torque acting about the shaft, even without rotation, can be taken out.). Suspending a shaft with a plurality of plate springs makes it possible to create a pseudo-rotating shaft. With a simple method, however, there is such a problem that the rotating shaft moves as the springs deform and torque stress accompanying rotation deviates greatly from linearity. Further, this places a limitation on heightening of the ratio of a stress coefficient relative to deformations in a direction of rotation and other directions, thus making it difficult to achieve high shaft precision.

Solution to Problem

As means to solve the foregoing problems, the present invention uses (1) a plurality of parallel springs and (2) a structure in which the length h and angle of each deformable side of each of the parallel springs are coincident with the distance h and direction from the rotating shaft center to a connecting point between the parallel spring and the rotating shaft. The use of the parallel spring structure makes it possible to apply high rigidity against deformations in directions other than the direction of rotation, and the coincidence of the lengths makes it possible to eliminate the movement of the shaft due to deformations of the parallel springs.

That is, the present invention is directed to a rotating shaft holding mechanism including a plurality of parallel spring links, each of the plurality of parallel spring links including: a movable side connected to a rotating shaft by a hinge at a connection point at a distance h radially away from a center of rotation of the rotating shaft; a plurality of deformable sides which are parallel to each other; hinges each of which connects one end of a corresponding one of the deformable sides to the movable side; and hinges each of which connects the other end of a corresponding one of the deformable sides to the stationary section, the effective length of each of the deformable sides being set to h to permit the rotating shaft, which is connected to the movable side by the hinge at the connecting point at the distance h radially away from the center of rotation of the rotating shaft, to rotate within a range of finite angles, the plurality of parallel spring links including at least two parallel spring links oriented in different directions.

Further, the rotating shaft holding mechanism of the present invention is configured such that a sum of spring constants of the hinges at both ends of each of the deformable sides is equal to a spring constant of the hinge at the connecting point.

Further, the rotating shaft holding mechanism of the present invention is configured such that the hinges at both ends of each of the deformable sides have a same spring constant and a same length L, and the hinge at the connecting point has a length 2L.

Further, the present invention is directed to a rotational viscometer including the rotating shaft holding mechanism, the rotating shaft holding mechanism being used as a holding mechanism of a torque measuring shaft of the rotational viscometer.

Advantageous Effects of Invention

A rotating shaft holding mechanism of the present invention makes it possible to achieve a high-precision bearing that is more compactible than a conventional ball bearing or air bearing, that is free of disturbances that would be cause by frictional resistance or a rolling motion of a rotating body in the case of a ball bearing, and that is free of the influence of air pressure that would be exerted in the case of an air bearing.

Further, the employment of a rotating shaft holding mechanism of the present invention in a bearing of a rotational viscometer makes it possible to achieve a compact, high-precision viscometer.

DESCRIPTION OF EMBODIMENTS

Figure 1:
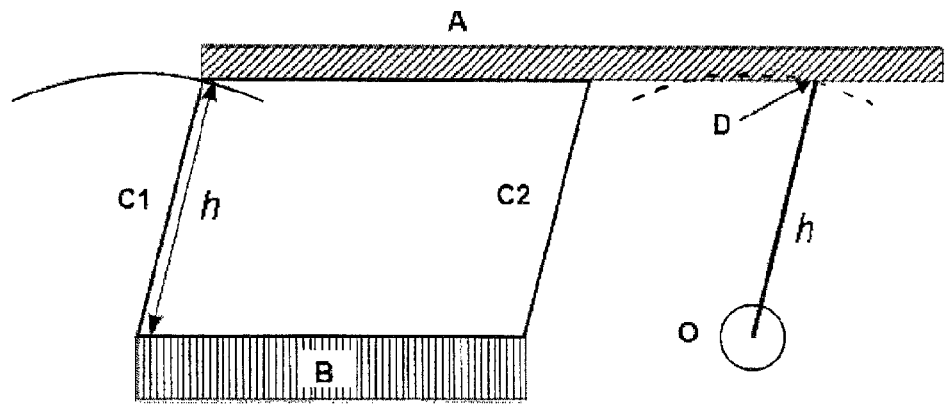
FIG. 1 is a conceptual diagram explaining a principle of a rotating shaft holding mechanism of the present invention.

FIG. 1 is a conceptual diagram for explaining a principle of a rotating shaft holding mechanism of the present invention.

Ideally, a parallel spring is structured such that only the angle of each vertex of a parallelogram varies. The parallel spring has one side fixed and two sides connected thereto, and deformation of the two sides translates the other one side. The parallel spring enables a very smooth movement by preventing an object from shifting, and as such, the parallel spring is used as a mechanism component where high-precision measurement is required. In detail, the motion of the movable side is a circular motion whose radius corresponds to the length of each deformable side, and a given point fixed on the movable side moves on the circumference centered at a point defined by the length and orientation of each deformable side. Therefore, a variable angle hinge placed at this position is found to serve as an element that constitutes the rotating shaft. The given point does not need to be on the movable side, but needs only be fixed at a position relative to the movable side. Theoretically, it does not matter how far the given point may be. This greatly improves the degree of freedom of structural design. However, since the angle of a hinge is a free angle, no rotating shaft can be defined with a single parallel spring. When hinges whose circular motions have their centers on the same axis are placed by parallel springs from two or more places, an object connecting these hinges to each other constitutes a rotating shaft that is coincident with the axis.

Let it be assumed in FIG. 1 that A denotes a movable side, B denotes a stationary section, C1 and C2 denote deformable sides, D denotes a hinge, and O denotes a rotating shaft (with no deformation between O and D). Then, the following statements hold true:

(1) The movable side A of the parallel spring draws an arc with a radius h.

(2) The hinge D, which joins the rotating shaft O and the movable side A, is provided at a point that, from a place that is supposed to be the center of the rotating shaft O, is coincident in inclination and length to the parallel spring. Then, O constitutes a rotating shaft that follows an arc motion of A. Since D is not limited in position, the position of the rotating shaft O can be freely set.

(3) With a single link to a rotating system by a parallel spring of FIG. 1, the position of O cannot by fixed by the hinge D. However, the position of the rotating shaft O can be determined by a combination of links by two or more parallel springs oriented in different directions.

The link of FIG. 1 has dealt with an ideal deformation in which only the vertices of a parallelogram deform. In actuality, however, the angle varies within a certain range of each deformable side. As a result, the effective length of each deformable side changes, and the movable side deviates from a circular motion. In the case of a parallel spring, parallelism can be kept by forming the deformable sides into identical shapes, but in the case of a rotational motion, a mechanism that compensates for a change in effective radius is necessary. In conclusion, assuming that the hinge section of each deformable side is a plate spring with a length L and the hinge forming the rotating shaft is a plate spring with a length 2L, a change in effective radius at a connecting point of the rotating shaft corresponds to a change in effective length of each deformable side. Further, in order to minimize the influence on the degree of freedom by the fact that the length of each hinge section is a finite length, the spring constant of the four hinges on the deformable sides and the hinge at the connecting point is set to 1:4, so that a structure is achieved in which both of the hinges exhibit homologous deformations.

When coupled by a plate spring, a deformable side appears to become longer by being tilted. This length effect can be compensated for by causing the length of the plate spring at the junction with the rotating shaft to match the total length of the plate springs at the two junctions of each deformable side.

In view of equilibrium of force, it is also necessary to cause the modulus of rotational elasticity of each of the plate spring of each deformable side to match the coefficient of the rotating shaft.

Figure 2:
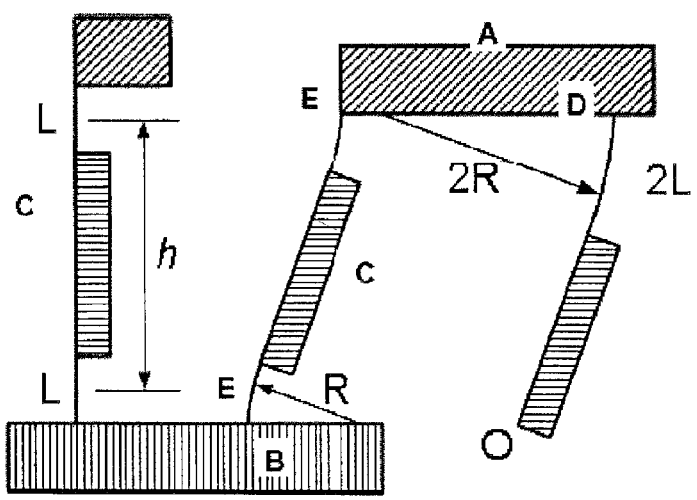
FIG. 2 is a theoretical explanatory diagram of optimization of a rotating shaft holding mechanism of the present invention.

FIG. 2 is a diagram for theoretically explaining optimization of deformation of a parallel spring of the present invention.

In FIG. 2, A denotes a movable side, B denotes a stationary section, C denotes deformable sides, D denotes a plate spring (hinge), and O denotes a rotating shaft. In FIG. 2, the left deformable side C is depicted as being in a yet-to-be-deformed state. In actuality, however, the left deformable side C deforms in a similar manner to the right deformable side C so that the two deformable sides C constitutes a parallelogram link.

Let it be assumed that at both ends of each of the deformable sides C, plate springs each with a length 2a (=L) bend in an arc by an angle $2\theta$. At this point in time, the vertices of the virtual parallelogram are on a line extending at an angle $\theta$ from the center point of the arc. The distance between this point and the connecting point can be expressed as $R \tan \theta$, where R is the radius of the arc. Since the actual length is $a = R\theta$, this difference appears as shifts. Since there is one hinge on the rotating shaft side, these shifts can be canceled out if the single hinge effects a change corresponding to that which is effected by the two deformable sides. This is achieved by simply making the effective length of the hinge at the connecting point twice as long (=2L), as θ is common. Assuming that no force is acting on the movable section (rotating shaft O) (i.e., under normal use), a force from the rotating shift and a force from the stationary section of the parallel spring balance each other. These forces act as bending moments of the hinge sections. While there are four hinges at the deformable sides, there is one hinge on the rotating shaft side. These hinges balance each other at the same bend angle. For that purpose, it is necessary that the spring constant of the hinge D on the rotating shaft side be four times greater than the spring constant of each of the hinges E at both ends of each of the deformable sides. (In a case where the spring constants are not coincident, the deformation is no longer an arc-like deformation, with the result that the shift from the ideal length is not accurately canceled out.)

EMBODIMENTS (Embodiment 1)

Figure 3:
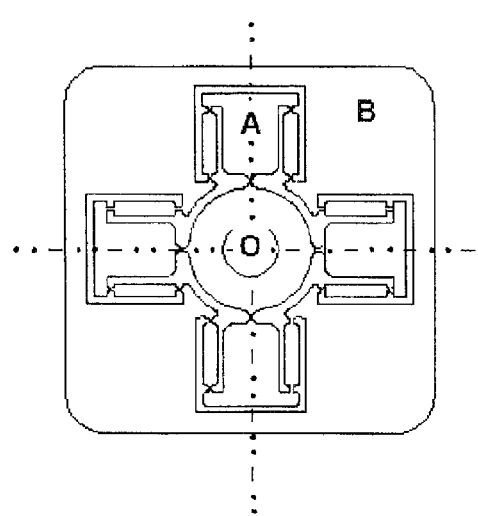
FIG. 3 is a diagram showing an embodiment of a rotating shaft holding mechanism of the present invention.
Figure 4:
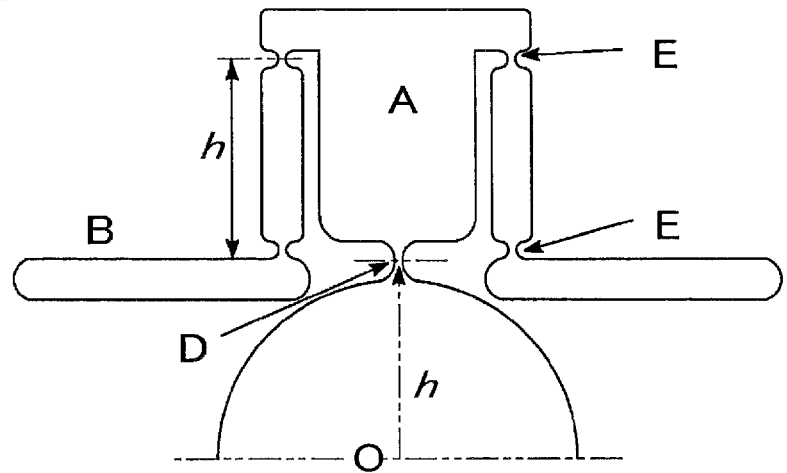
FIG. 4 is a partially-enlarged view of a main part of the embodiment.

FIG. 3 is a diagram showing an embodiment of a rotating shaft holding mechanism of the present invention. FIG. 4 is a partially-enlarged view of a main part of the embodiment.

FIG. 3 shows an example where a rotating shaft holding mechanism of the present invention is achieved by wire-cut processing or the like. In the example shown in FIG. 3, four links each formed by a parallel spring are placed at intervals of 90 degrees. In FIG. 3, A denotes a movable section of each of the parallel springs, B denotes a stationary section of each of the parallel springs, and O denotes a rotating shaft. FIG. 4 is an enlarged view of one of the four parallel spring links shown in FIG. 3. In FIG. 4, A denotes the movable section of the parallel spring, B denotes the stationary section of the parallel spring (drawn in simpler form for convenience of explanation, albeit not coincident in shape with that shown in FIG. 3), D denotes a hinge, E denotes hinges of the parallel spring, and O denotes the shaft.

The hinge section D is twice larger in wire-cut radius than each of the hinge sections E. Further, the hinge section D is also twice larger in thickness than each of the hinge sections E. When the link formed by the parallel spring rotates by a radius h, a given point on the movable section A similarly rotates by the radius h, and the hinge D provided on the movable section A rotates by the radius h, too. At this point in time, since the hinge D is provided in a position at a distance h from the center of rotation of the shaft O, the shaft O naturally rotates so that the center of rotation does not become misaligned. The range of finite angles within which rotation is possible corresponds to the range of movement of the parallel spring. In this example, the range of finite angles within which rotation is possible is approximately ±0.1 radian.

For the purpose of reducing stress torque with respect to rotation, for example, it is also possible to produce the hinge section from a plate spring.

In the example shown in FIG. 3, a total of four links each formed by a parallel spring are placed at intervals of substantially 90 degrees around the shaft. However, the center of the shaft can be defined simply by placing at least two such links at different angles. For example, it is possible to place three such links at intervals of 120 degrees instead of placing four such links at intervals of 90 degrees. Alternatively, it is possible to provide a parallel spring so that the parallel spring is shifted in a direction along the shaft. For example, it is possible to provide a total of four parallel springs, two placed at intervals of 180 degrees around the shaft, another two placed at intervals of 180 degrees in a position shifted in a direction along the shaft.

(Embodiment 2)

Since a rotating shaft holding mechanism of the present invention has a parallel spring structure, there is theoretically a proportional relationship between the torque and the angle of rotation. Therefore, it can be used in a torque meter by measuring the angle of rotation. Utilizing this makes it possible to serve as a torque measurement unit of a rotational viscometer. Alternatively, it can be used in a torque meter by, when the torque measuring shaft is rotationally displaced, applying, to the torque measuring shaft, torque that cancels out the rotational displacement and calculating the value of the torque applied.

Figure 5:
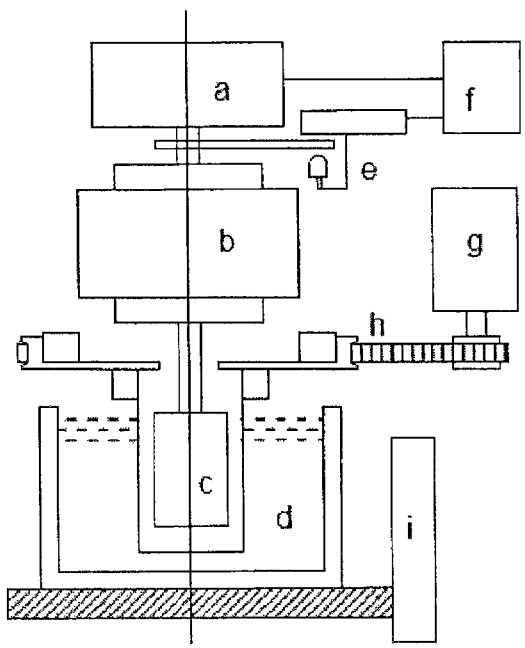
FIG. 5 is a rotational viscometer using a conventional air bearing.

FIG. 5 shows a conventional rotational viscometer (of a coaxial bicylindrical type). In FIG. 5, a, e, and f denote a torque detection mechanism, b denotes an air bearing, c denotes inner and outer cylinders, d denotes a constant-temperature bath, g and h denote a rotating mechanism of the outer cylinder, and i denotes a raising and lowering mechanism of the constant-temperature bath. In the rotational viscometer of FIG. 5, the cylindrical shaft (outer cylinder) that causes rotation and the cylindrical shaft (inner cylinder) that measures torque are different, and the rotation shaft on the side of the inner cylinder hardly rotates. However, in order to accurately measure torque acting on a shaft, an air bearing has been used, as it is small in load change of rotation.

In view of this, the present invention replaces the conventional air bearing b with a rotating shaft holding mechanism of Embodiment 1 to provide a rotational viscometer that is excellent both in terms of cost and handleability.

A torque meter of a rotational viscometer thus obtained can make the shaft highly rigid and the inertia moment small, and as such, is ideal as a torque meter of a rotational viscometer. This makes it possible to widen the range of measurement. Since the inertia moment is small, the response speed rises and, in particular, contributions are made to the expansion of the frequency domain of a rheometer. In a high-precision rotational viscometer, an expensive air bearing has been used to hold the torque measuring shaft. However, replacing the air bearing with a rotating shaft holding mechanism of the present invention offers prospects for improvement not only in cost but also in performance, reduction of maintenance, and improvement in handleability.

Industrial Applicability

As an application of a rotating shaft holding mechanism of the present invention, an example of a rotational viscometer has been described in Embodiment 2. However, the rotating shaft holding mechanism of the present invention is also applicable to another device that has a rotating shaft.

The invention claimed is:

1. A rotating shaft holding mechanism including a plurality of parallel spring links, each of the plurality of parallel spring links comprising:
   a movable side connected to a rotating shaft by a hinge at a connection point at a distance h radially away from a center of rotation of the rotating shaft;
   a plurality of deformable sides which are parallel to each other;
   hinges each of which connects one end of a corresponding one of the deformable sides to the movable side; and
   hinges each of which connects the other end of a corresponding one of the deformable sides to the stationary section,
the effective length of each of the deformable sides being set to h to permit the rotating shaft, which is connected to the movable side by the hinge at the connecting point at the distance h radially away from the center of rotation of the rotating shaft, to rotate within a range of finite angles, the plurality of parallel spring links comprising at least two parallel spring links oriented in different directions.

2. The rotating shaft holding mechanism as set forth in claim 1, wherein a sum of spring constants of the hinges at both ends of each of the deformable sides is equal to a spring constant of the hinge at the connecting point.

3. The rotating shaft holding mechanism as set forth in claim 2, wherein the hinges at both ends of each of the deformable sides have a same spring constant and a same length L, and the hinge at the connecting point has a length 2L.

4. A rotational viscometer comprising a rotating shaft holding mechanism as set forth in claim 1, the rotating shaft holding mechanism being used as a holding mechanism of a torque measuring shaft of the rotational viscometer.

* * * * *